United States Patent [19]

Komatsu

[11] Patent Number: 4,641,084
[45] Date of Patent: Feb. 3, 1987

[54] ION CONCENTRATION MEASURING APPARATUS

[75] Inventor: Satsuki Komatsu, Sagamihara, Japan

[73] Assignee: Olympus Optical Co., Ltd., Tokyo, Japan

[21] Appl. No.: 677,865

[22] Filed: Dec. 4, 1984

[30] Foreign Application Priority Data

Dec. 15, 1983 [JP] Japan ................. 58-235134

[51] Int. Cl.$^4$ .................. G01N 27/02; G01N 27/26
[52] U.S. Cl. ..................... 324/71.5; 324/439; 204/406
[58] Field of Search ............ 324/71.5, 425, 439, 324/71.1, 438; 357/23.13; 204/406

[56] References Cited

U.S. PATENT DOCUMENTS

| | | | |
|---|---|---|---|
| 3,648,159 | 3/1972 | Stansell et al. | 324/438 |
| 4,332,658 | 6/1982 | Tsuboshima | 357/25 X |
| 4,385,274 | 5/1983 | Shimada et al. | 357/25 X |
| 4,444,644 | 4/1984 | Hiramoto et al. | 357/25 X |
| 4,490,216 | 12/1984 | McDonnell | 357/25 X |

Primary Examiner—Reinhard J. Eisenzopf
Assistant Examiner—Robert W. Mueller
Attorney, Agent, or Firm—Parkhurst & Oliff

[57] ABSTRACT

An apparatus for measuring a concentration of a specific ion contained in a test liquid held in a container with the aid of a reference electrode and an ion sensitive field effect transistor having a gate portion selectively sensitive to the specific ion, including a series circuit of a reference resistor and a constant voltage supply source connected across drain and source of the ion sensitive field effect transistor, a potential control circuit having inputs connected across the reference resistor to detect a potential difference across the reference resistor for controlling a source or drain potential of the ion sensitive field effect transistor in such a manner that the potential difference remains at a predetermined value and a voltmeter for measuring the source or drain potential as a measure of the ion concentration.

8 Claims, 2 Drawing Figures

ION CONCENTRATION MEASURING APPARATUS

BACKGROUND OF THE INVENTION

The present invention relates to an ion concentration measuring apparatus comprising a semiconductor ion sensor.

A semiconductor ion sensor utilizing a field effect in a semiconductor body has been developed and is called Ion Sensitive Field Effect Transistor (ISFET). Such an ISFET has been disclosed in Japanese Patent Application Laid-open Publications Nos. 139,289/76 and 26,292/77. In ISFET, on a gate of an insulated gate field effect transistor manufactured by a well developed IC technique, is formed a chemical selective film containing ion-exchange substances or enzymes, and a potential at an interface between the chemical selective film and an electrolyte is detected to measure specific ion concentration and substances acting upon the enzymes in the electrolyte.

The ion concentration measuring apparatus comprising the above mentioned ISFET has been disclosed in, for instance, Japanese Patent Application Laid-open Publication No. 136,396/79.

FIG. 1 is a schematic view showing the above mentioned known ion concentration measuring apparatus, in which a bias voltage applied to a reference electrode is so controlled that a given constant current flows between the source and drain of an ISFET sensitive to specific ion in a test liquid, and then a concentration of the specific ion and an ion activity are detected in accordance with said bias voltage value. In FIG. 1, a container 1 contains a test liquid 2 and an ISFET 3 is immersed in the test liquid 2 together with a reference electrode 5 in such a manner that at least a gate portion 4 of ISFET 3 is made in contact with the test liquid 2. Between a drain electrode 6 of ISFET 3 and the earth is connected a constant voltage supply source 7, and a source electrode 8 and a semiconductor substrate 9 of ISFET 3 are connected via a reference resistor 10 to the earth. The reference electrode 5 is connected to a potential control circuit 11 including a bias voltage source, by means of which the bias voltage is so controlled that the potential of the source electrode 8 is set to a predetermined value and thus a predetermined current flows between the source and drain. Then the voltage value across outputs 12 and 13 is measured with the aid of a voltmeter such as a valve voltmeter.

In principle, the drain current of the FET is changed in accordance with two factors, i.e. the voltage across the drain and source and the voltage across the gate and source. Further, if the voltage across the drain and source is always maintained above a certain level, the drain current is substantially proportional to the voltage across the gate and source. Such an operating region is called a saturation region. In the ion concentration measuring apparatus shown in FIG. 1, the ISFET 3 is operated in the saturation region and thus the drain current is determined by the voltage across the gate and source.

In FIG. 1, the gate potential $V_G$ of ISFET 3 is equal to a sum of a potential $E_R$ of the test liquid 2 set by the reference electrode 5 and an interface potential $E_G$ generated at the chemically sensitive film of the gate portion 4 in response to the ion activity of specific ion in the test solution 2 ($V_G = E_R + E_G$). Further, if it is assumed that a resistance value of the resistor 10 is R, the voltage of the constant voltage supply source is $E_B$ and the drain current is $I_D$, then the voltage $V_{DS}$ across the drain and source may be expressed by $V_{DS} = E_B - I_D R$. Then, a deviation $dI_D$ of the drain current $I_D$ may be represented as follows.

$$dI_D = \frac{\partial I_D}{\partial V_{DS}} dV_{DS} + \frac{\partial I_D}{\partial V_G} dV_G$$

As explained above, when the ISFET 3 is driven in the saturation region, the change in the voltage $V_{DS}$ across the drain and source does not have any influence upon the drain current $I_D$. Therefore, in the above equation, it becomes $$\frac{\partial I_D}{\partial V_{DS}} = 0,$$

and $$dI_D = \frac{\partial I_D}{\partial V_G} d(E_R + E_G)$$

is obtained. That is to say, when $E_R + E_G$ is constant, the drain current $I_D$ is kept also constant.

In the saturation region, when the ion activity of the test liquid 3 varies, the interface potential $E_G$ at the chemically selective film of the gate portion 4 is changed into $E_G + \Delta E_G$, and thus the drain current $I_D$ is varied. Therefore, the voltate $I_D R$ across the reference resistor 10 is also changed. The potential control circuit 11 operates to adjust the potential $E_R$ of the test liquid 2 via the reference electrode 5 in such a manner that the drain current $I_D$ remains at the given value. In this case, the variation $\Delta E_R$ of the potential of the test liquid 2 serves to change from $dI_D = 0$ to $\Delta(E_R + E_G) = 0$, and therefore, $\Delta E_R = -\Delta E_G$. By measuring the variation $\Delta E_R$ of the potential of the test liquid 2, i.e. the variation of the potential at the reference electrode 5 across the outputs 12 and 13, it is possible to detect $-\Delta E_G$, so that the variation in the ion activity can be derived therefrom.

In the ion concentration measuring apparatus shown in FIG. 1, since the ISFET 3 is driven by the constant voltage, an electrical overload condition does not occur and thus the operation is stable. However, since the variation in the ion activity is detected by changing the potential $E_R$ of the test liquid 2, it is absolutely necessary to electrically isolate the container 1 in a positive manner and it is principally impossible to simultaneously effect measurements with the aid of a plurality of ISFETs.

SUMMARY OF THE INVENTION

The present invention has for its object to provide an ion concentration measuring apparatus in which an ion concentration can be measured while a potential of a test liquid is maintained constant.

It is another object of the invention to provide an ion concentration measuring apparatus in which simultaneous measurements with the aid of a plurality of IS-FETs can be performed, while a potential at a test liquid remains constant.

According to the invention, an ion concentration measuring apparatus comprises a container for holding a test liquid containing at least one kind of ion whose concentration is to be measured;

means contacted with the test liquid for maintaining the test liquid at a constant potential;

at least one ion sensitive field effect transistor having a gate portion which is selectively sensitive to the ion, drain and source;

at least one measuring circuit comprising a constant voltage supply source which is not connected to the earth and which applies a constant voltage across the drain and source of the ion sensitive field effect transistor, a reference resistor connected across the constant voltage supply source and the drain or source, a potential control circuit having inputs connected across the reference resistor and an output connected to the drain or source for controlling a potential at the drain or source in such a manner that a voltage across the reference resistor retains a predetermined value, and a voltmeter for measuring a variation of the potential at the drain or source as a measure of the concentration of ion.

DESCRIPTION OF THE DRAWINGS

FIG. 3 is a schematic view depicting another embodiment of the ion concentration measuring apparatus according to the invention.

DESCRIPTION OF THE PREFERRED EMBODIMENTS

Figure 1:
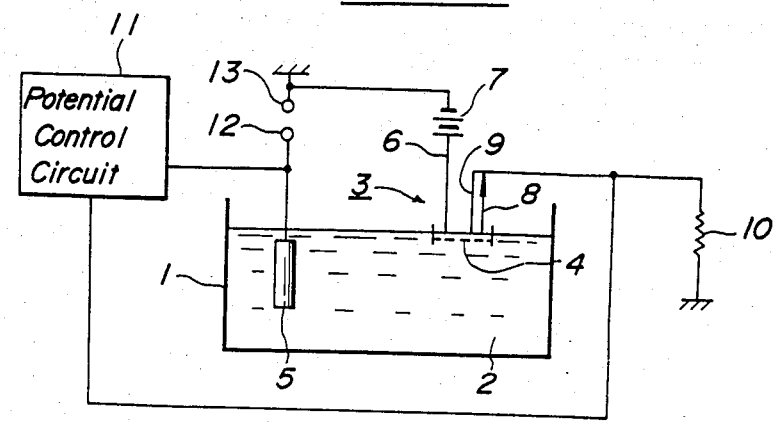
FIG. 1 is a schematic view showing a known ion concentration measuring apparatus.
Figure 2:
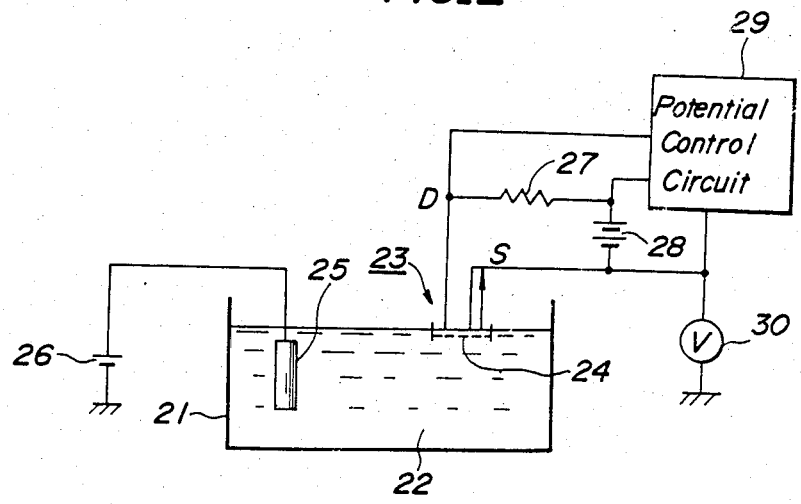
FIG. 2 is a schematic view illustrating a construction of an embodiment of the ion concentration measuring apparatus according to the invention.

FIG. 2 is a schematic view showing an embodiment of the ion concentration measuring apparatus according to the invention. In the present embodiment, a container 21 contains a test liquid 22 including a specific ion whose concentration is to be measured. An ISFET 23 sensitive to the specific ion is immersed into the test liquid 22 together with a reference electrode 25 in such a manner that at least a gate portion 24 thereof is made in contact with the test liquid 22. The reference electrode 25 is connected to a constant voltage supply source 26 for maintaining the test liquid 22 at a predetermined potential. Across a drain (D) and a source (S) of ISFET 23 is connected a series circuit of a reference resistor 27 and a constant voltage supply source 28 so as to apply such a constant voltage that ISFET 23 operates in a saturation region. A potential difference across the reference resistor 27 is detected by a potential control circuit 29. In the present embodiment, the potential control circuit 29 controls a potential at the source S of ISFET 23 in such a manner that the potential difference, i.e. the drain current is maintained at a predetermined value. In this manner, a variation in an interface potential at the gate portion 24 of ISFET 23 due to the ion activity can be detected as a variation in the source potential. Therefore, by detecting the variation in the source potential with the aid of a voltmeter 30, it is possible to measure the ion concentration.

FIG. 3 is a schematic view illustrating another embodiment of the ion concentration measuring apparatus according to the invention. In the present embodiment, concentrations of three different kinds of ions in a test liquid 32 contained in a container 31 are to be simultaneously measured. For this purpose, in the test liquid 32 are immersed three ISFETs 33a, 33b and 33c having gate portions 34a, 34b and 34c, respectively which are selectively sensitive to respective one of the three kinds of ions. These ISFETs may be formed on the same semiconductor substrate. Further a reference electrode 35 is also immersed in the test liquid 32. The reference electrode 35 is connected to a constant voltage supply source 36 so as to maintain the test liquid 32 at a given potential. Across drains and sources of respective ISFETs 33a, 33b and 33c are connected series circuits of reference resistors 37a, 37b and 37c and constant voltage supply sources 38a, 38b and 38c, respectively, so that the ISFETs 33a, 33b and 33c are biased to operate in the saturation condition. Across respective reference resistors 37a, 37b and 37c are connected potential control circuits 39a, 39b and 39c, respectively, which control source potentials of respective ISFETs 33a, 33b and 33c in such a manner that the potential differences across the reference resistors 37a, 37b and 37c are maintained at predetermined values. Then, the concentrations of specific ions can be measured simultaneously by detecting the variations of the source potentials with the aid of voltmeters 40a, 40b and 40c, respectively.

The present invention is not limited to the embodiments explained above, but various modifications and alternations may be conceived by those skilled in the art within the scope of the invention. For instance, the reference resistor may be connected to the source instead of the drain side. Further, the control for maintaining the potential difference across the reference resistor, i.e. the current passing between the drain and source to the predetermined value may be effected by changing the drain potential instead of the source potential. In such a case, it is matter of course to detect the change of the drain potential to measure the ion concentration. Moreover, in case of using a plurality of ISFETs, they may be formed on separate substrates or they may respond to the same ion. In the latter case, the ion concentration may be derived as an average of a plurality of measured values.

According to the invention, since the ISFET is operated in the constant mode, while the potential of the test liquid remains constant, stable operation can be attained and the small variation of the interface potential in accordance with the ion activity can be detected in a very precise manner. Further, since the test liquid is maintained at a constant potential, it is possible to use simultaneously a plurality of ISFETs which respond to the same ion or different kinds of ions. In the former case, it is possible to obtain an average value of ion concentrations measured by respective ISFETs in a simple manner. In the latter case, it is possible to derive a plurality of ion concentrations of different kinds of ions simultaneously. In either case, it is possible to shorten the measuring time materially. Furthermore, the reference electrode may be connected to the earth. In this case, if the container is made of conductive material and is connected to the earth, the reference electrode may be dispensed with. In this manner, the whole construction may be made much simpler.

What is claimed is:

1. An ion concentration measuring apparatus comprising:
    a container for holding a test liquid containing at least one kind of ion whose concentration is to be measured;
    means in contact with the test liquid for maintaining the test liquid at a constant potential;
    at least one ion sensitive field effect transistor having a gate portion which is selectively sensitive to said ion, drain and source;

at least one measuring circuit comprising a constant voltage supply source which is not connected to the earth and which applies a constant voltage across the drain and source of the ion sensitive field effect transistor, a reference resistor connected to the constant voltage supply source and the drain or source, a potential control circuit having inputs connected across the reference resistor and an output connected to the drain or source for controlling a potential at the drain or source in such a manner that a voltage across the reference resistor remains a predetermined value, and a voltmeter for measuring a variation of the potential at the drain or source as a measure of the concentration of ion.

2. An apparatus according to claim 1, wherein the apparatus comprises a plurality of ion sensitive field effect transistors each having gate portions sensitive to different kinds of ions contained in the test liquid and a plurality of measuring circuits each connected to respective ion sensitive field effect transistors, whereby concentrations of the different kinds of ions are measured simultaneously.

3. An apparatus according to claim 2, wherein said plurality of ion sensitive field effect transistors are formed on the same substrate.

4. An apparatus according to claim 2, wherein said plurality of ion sensitive field effect transistors are formed on separate substrates.

5. An apparatus according to claim 1, wherein the apparatus comprises a plurality of ion sensitive field effect transistors having gate portions sensitive to the same ion in the test liquid and a plurality of measuring circuits each connected to respective ion sensitive field effect transistors, whereby a plurality of concentrations of the same ion are derived simultaneously.

6. An apparatus according to claim 1, wherein said means for maintaining the test liquid at the constant potential comprises a reference electrode immersed in the test liquid and a constant voltage supply source connected to the reference electrode.

7. An apparatus according to claim 1, wherein said means for maintaining the test liquid at the constant potential comprises a reference electrode immersed in the test liquid and means connecting the reference electrode to the earth.

8. An apparatus according to claim 1, wherein said container is made of an electrically conductive material, and said means for maintaining the test liquid at the constant potential comprises means connecting the container to the earth.

* * * * *